United States Patent [19]

Yewer, Jr.

[11] Patent Number: 5,581,810

[45] Date of Patent: *Dec. 10, 1996

[54] THREE DIMENSIONAL FABRIC SUPPORT BELT

[76] Inventor: Edward H. Yewer, Jr., 6259 N. Highway 83, Hartland, Wis. 53029

[*] Notice: The term of this patent shall not extend beyond the expiration date of Pat. No. 5,432,951.

[21] Appl. No.: 499,878

[22] Filed: Jul. 10, 1995

Related U.S. Application Data

[63] Continuation of Ser. No. 56,342, Apr. 30, 1993, Pat. No. 5,432,951.

[51] Int. Cl.⁶ .............................. A61F 9/00; A61F 5/00; A61F 5/37
[52] U.S. Cl. ........................ 2/44; 2/311; 602/19
[58] Field of Search ...................... 2/300, 308, 309, 2/310, 311, 312, 313, 314, 315, 338, 44, 92; 139/387 R, 384 R; 602/19

[56] References Cited

U.S. PATENT DOCUMENTS

| | | | |
|---|---|---|---|
| 1,310,271 | 7/1919 | Achtmeyer | 2/338 |
| 2,396,329 | 3/1946 | Lipmann | 2/338 |
| 2,502,101 | 3/1950 | Morgan et al. | 139/384 R |
| 3,009,232 | 11/1961 | Martin | 139/384 R |
| 3,530,031 | 9/1970 | Loew | 2/338 |
| 4,561,128 | 12/1985 | Zimmerman | 2/275 |
| 4,782,535 | 11/1988 | Yewer, Jr. et al. | 2/321 |
| 5,036,864 | 8/1991 | Yewer, Jr. | 128/876 |
| 5,178,163 | 1/1993 | Yewer, Jr. | 128/876 |

*Primary Examiner*—Jeanette E. Chapman
*Attorney, Agent, or Firm*—Quarles & Brady

[57] ABSTRACT

A support belt has a core layer made of a three dimensional fabric in which a cushion layer has a serpentine undulating cross-sectional shape in at least one dimension so as to define peaks and valleys which space inner and outer surfaces of the core such that the thickness of the core at a given location is greater than the sum of the thicknesses of threads of the fabric at that location. The core may have multiple cushion layers and may be covered with a closed weave fabric on one or both sides thereof. Preferably, a strap encircles the core and a buckle is provided for adjustably securing the strap around a body with the core between the strap and the body.

2 Claims, 3 Drawing Sheets

FIG. 3
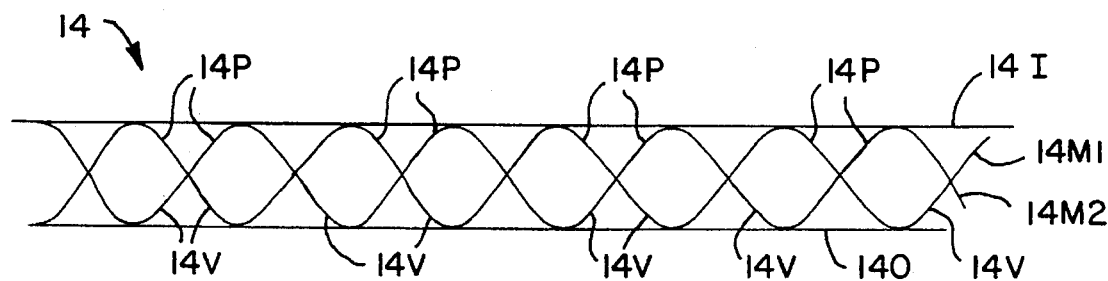
FIG. 4
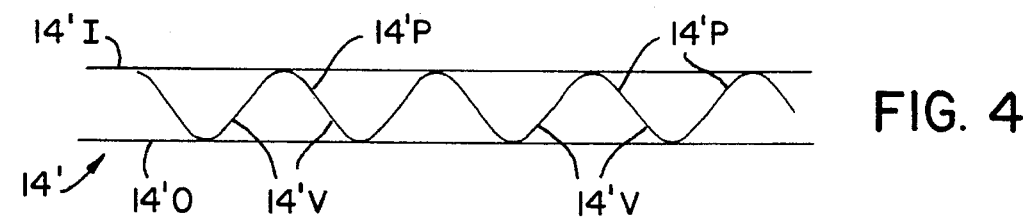
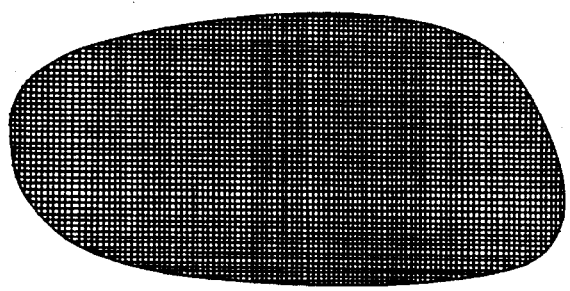
FIG. 5
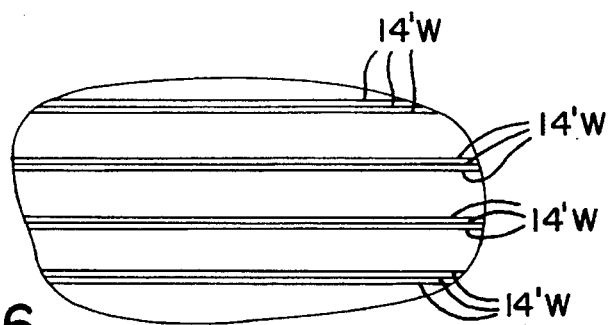
FIG. 6

THREE DIMENSIONAL FABRIC SUPPORT BELT

This is a continuation of application Ser. No. 08/056,342 filed Apr. 30, 1993, now U.S. Pat. No. 5,432,951.

FIELD OF THE INVENTION

This invention relates to a support belt intended to be secured around the waist of a human user's body.

BACKGROUND OF THE INVENTION

It is well known that a support belt may be secured around a human user's waist with the effect of increasing the user's strength and load carrying ability, relieving back pain, and other benefits. However, there is a concentration of sweat glands in the abdominal area of the waist where such belts are usually secured which can generate a significant volume of perspiration, and thus that area serves an important purpose for proper cooling of the human body.

Traditionally, support belts have been made of relatively heavy and stiff natural materials, usually leather. An improved belt, made of synthetic materials laminated together is described in U.S. Pat. No. 4,782,535 issued Nov. 8, 1988. In this belt, an inner fabric layer, an intermediate foam layer, and an outer fabric layer are laminated together and a high strength nylon strap is wrapped around the lamination and secured thereto. A buckle is provided to secure the ends of the strap so as to hold the belt around the waist of a user. An improved buckle structure for securing such a belt is described in U.S. Pat. No. 5,036,864, issued Aug. 6, 1991.

Prior belts, while having desirable strength and stiffness characteristics, have in general been made of closed, relatively unbreathable materials. Such belts have not allowed for significant ventilation or perspiration drainage or evaporation of the abdominal area encompassed by the belt and therefore have been hot under some circumstances for the user to wear.

A belt addressing these problems is disclosed in U.S. Pat. No. 5,178,163 which issued Jan. 12, 1993. The belt disclosed in this patent is of the same basic construction as the belt disclosed in U.S. Pat. No. 4,782,535, but the intermediate foam layer is perforated to provide ventilation and drainage from the inner fabric layer to the outer fabric layer. While the disclosed construction affords significant advantages, room still exists for improvement. In particular, it is desired to reduce the weight of the belt and increase the ventilation through the belt, while maintaining the strength and stiffness characteristics which are important in belts of this type.

SUMMARY OF THE INVENTION

The invention provides a support belt having a core layer made of a three dimensional fabric in which a cushion layer has a serpentine undulating cross-sectional shape in at least one dimension so as to define peaks and valleys which space inner and outer surfaces of the core such that the thickness of the core at a given location is greater than the sum of the thicknesses of threads of the fabric at that location. The three dimensional shape of the core imparts to the belt strength and stiffness characteristics which are desirable in belts of this type while the core can be made light in weight and breathable. In this regard, it is especially preferred that the fabric of the core be of an open weave.

In a preferred aspect, the core may have multiple cushion layers, preferably interwoven with one another, to impart additional strength to the belt, and may have facing layers interwoven with the cushion layers so as to present a substantially flat surface of the core. This helps to uniformly distribute loads over the area of the facing layer when the belt is cinched around a body.

The core may also be covered with a closed weave fabric on one or both sides thereof for comfort if the belt is to be worn next to a user's skin or for aesthetics in the case of an outer fabric covering. In one embodiment, no fabric coverings are provided over the core to maximize ventilation and minimize weight.

The core is preferably made of synthetic threads which are relatively stiff as compared to natural fibers. In addition, synthetic thermoplastic fibers can be heat sealed together so as to prevent unravelling at any cut edges of the core. A binding strip is preferably secured by sewing or gluing around the edges of the belt for comfort to prevent direct contact between edges of the core and the user and for aesthetics. Synthetic threads can also be adhered in a hot or cold lamination process to any fabric layers applied over the surfaces of the core.

Preferably, a strap encircles the core and a buckle is provided for adjustably securing the strap around a body with the core between the strap and the body. The strap is made of high tensile strength materials and therefore allows tight cinching of the belt around the body without subjecting the core to tensile cinching forces which could otherwise damage it.

BRIEF DESCRIPTION OF THE DRAWINGS

FIG. 3 is a top cross-sectional schematic view illustrating a core layer of three dimensional fabric for the belt of FIG. 1;

FIG. 4 is a top cross-sectional schematic view illustrating a core layer of three dimensional fabric for the belt of FIG. 2;

FIG. 5 is a frontal elevation view illustrating a grid type thread pattern as used in the two facing layers of the core shown in FIG. 3 and as used in the inner facing layer of the core shown in FIG. 4;

FIG. 6 is a frontal elevation view illustrating the thread pattern of the outer facing layer of the core shown in FIG. 4;

DETAILED DESCRIPTION OF THE PREFERRED EMBODIMENTS

Figure 1:
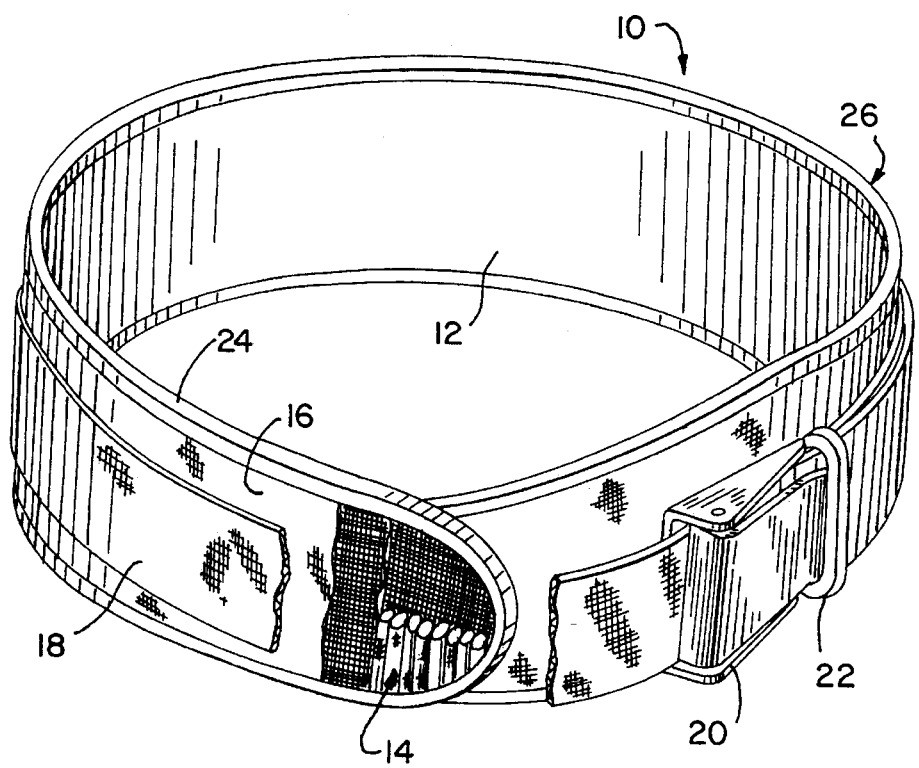
FIG. 1 is a perspective view of a support belt of the invention with portions broken away.

Referring to FIG. 1, a support belt 10 of the invention has an inner fabric layer 12, an intermediate core layer 14, an outer fabric layer 16, a strap 18, a buckle 20 and a torque ring 22. An edge binding strip 24 is stitched along the edge of the belt 10. It would also be possible, of course, to secure the binding strip 24 to the edge of the belt 10 by a suitable adhesive, either hot or cold.

The buckle 20 and torque ring 22 used in the preferred embodiment 10 are disclosed in U.S. Pat. No. 5,036,864, the disclosure of which is hereby incorporated by reference. The fabric layers 12 and 16, binding strip 24 and strap 18 may be made of the same materials and stitched together in the same way as described in U.S. Pat. No. 5,178,163, the disclosure of which is hereby incorporated by reference.

What differs about the belt 10 from the prior belts is the use of a three dimensional fabric core 14, whereas in the prior belts the core layer was made of foam. As used herein, the term three dimensional fabric means a fabric in which the thickness of the fabric at a particular location is greater than the sum of the thicknesses of the threads of the layers of the fabric at that location. The thickness is defined as the distance from one surface of the fabric to the opposite surface of the fabric when the fabric is in its natural state, so that the layers of the fabric are together but not so that the fibers of the layers of the fabric are compressed or deformed. Laying the fabric flat on a table with one surface of the fabric against the table surface and so as to remove wrinkles from the fabric places the fabric in its natural state.

Figure 2:
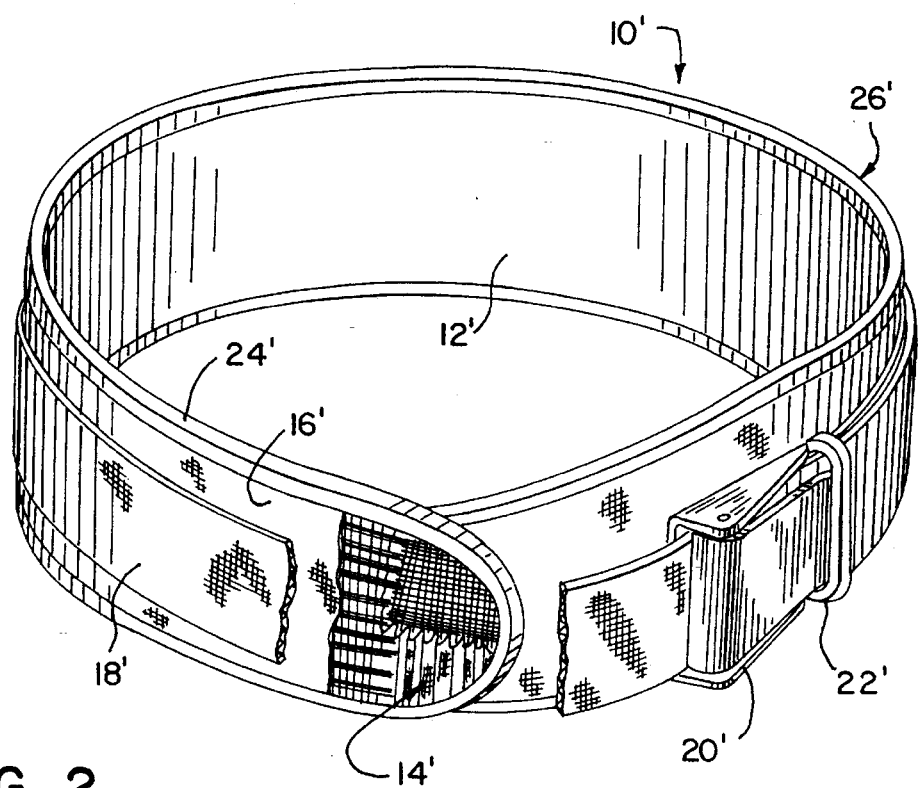
FIG. 2 is a perspective view of a second embodiment of a support belt of the invention with portions broken away.

FIG. 2 illustrates an alternate support belt 10' of the invention which is identical in all respects to the support belt 10 except for having a core 14' which is three dimensional fabric of a different type than the fabric used in the belt 10. In FIG. 2, elements corresponding to the elements shown in FIG. 1 are identified by the same reference numbers followed by a prime (') sign.

Referring to FIGS. 3 and 4, top cross-sectional views of the cores 14 and 14' are shown respectively. Referring to FIG. 3, the core 14 has an inner facing layer 14I, two cushion or middle layers 14M1 and 14M2 and an outer facing layer 14O. The core 14' shown in FIG. 4 has an inner facing layer 14'I and an outer facing layer 14'O (in 14O and 14'O, the "O" is the letter "O", not not a zero), but only one cushion layer 14'M. In each of the cores 14 and 14', the cushion layers define peaks 14P and 14'P and valleys 14V and 14'V. Each peak 14P is interwoven with the inner facing layer 14I, each valley 14V is interwoven with the outer facing layer 14O, each peak 14'P is interwoven with the inner facing layer 14'I and each valley 14'V is interwoven with the outer facing layer 14'O in the manner hereinafter described. In addition, in the core 14 which has two cushion layers 14M1 and 14M2, the two cushion layers 14M1 and 14M2 intersect at junctures 14J where the warp threads of each layer 14M1 and 14M2 pass through the interstitial spaces of the other cushion layer.

FIG. 5 illustrates the thread pattern of all of the layers of the cores 14 and 14' shown in FIGS. 3 and 4 except for the layer 14'O. Thus, all of the layers except 14'O are woven, having warp and fill threads woven together. The layer 14'O is shown in FIG. 6, and has no fill threads, having only warp threads 14'W arranged in spaced apart bundles of three threads per bundle. It should be noted that in fabrics of the type shown in FIGS. 5 and 6, the fill threads of the facing layers may not be straight in the areas between the peaks and valleys, but may be rather wavy.

Figure 7:
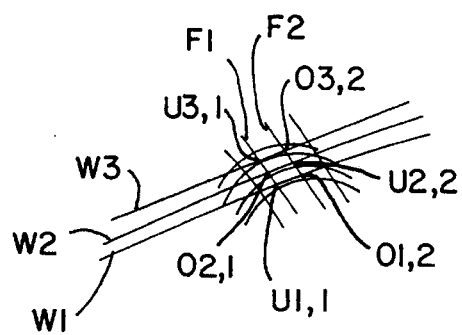
FIG. 7 is a partial perspective view illustrating how the peaks and valleys of the core shown in FIG. 3 and the peaks of the core shown in FIG. 4 are woven respectively with the inner and outer facing layers in FIG. 3 and with the inner facing layer in FIG. 4.

FIG. 7 illustrates the weaving pattern of the peaks 14P and layer 14I, of the valleys 14V and layer 14O, and of the peaks 14'P and the layer 14'I. For the two fill threads F1 and F2 which are at the top of the respective peak 14P or 14'P or bottom of the respective valley 14V, the warp threads in the adjacent facing layer alternate in the weave pattern between the fill threads. For example, as shown in FIG. 7, warp thread W1 goes under fill thread F1 at intersection U1,1 and goes over fill thread F2 at intersection O1,2. The adjacent warp thread W2 goes over fill thread F1 at intersection O2,1 and goes under fill thread F2 at intersection U2,2. Warp thread W3, like warp thread W1, goes under fill thread F1 (at intersection U3,1) and over fill thread F2 (at intersection O3,2).

Figure 8:
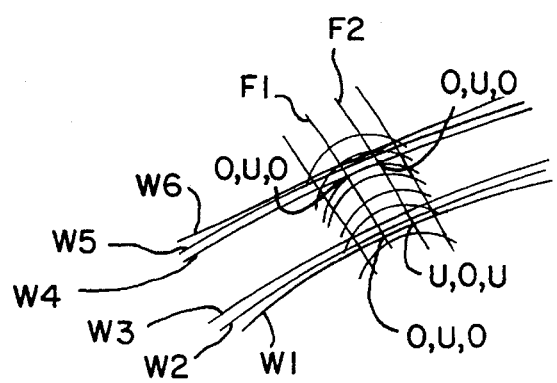
FIG. 8 is a perspective view illustrating how the valleys of the core shown in FIG. 4 are woven with the outer facing layer of threads of the core shown in FIG. 4.

FIG. 8 illustrates the intersections of the threads of layer 14'O with the layer 14'M of FIG. 4. It is noted that in FIG. 7, each separate warp thread is threaded through only one interstitial space in each row of interstitial spaces, whereas in FIG. 8, three warp threads extend through a single interstitial space. In FIG. 8, the warp threads W1-3 alternate in their weave pattern relative to fill threads F1 and F2 as indicated by the notations O,U,O (over, under, over) and U,O,U (under, over, under) which indicate the intersections of the respective warp threads W1, W2, W3 and W4, W5, W6 with the fill threads F1 and F2.

A preferred fabric for the core 14 illustrated in FIG. 3 has cushion layers 14M1 and 14M2 with the warp threads spaced at approximately 18 warp threads per inch and each warp thread being a 0.020 inch diameter polypropylene filament. The fill threads in each cushion layer 14M1 and 14M2 are also spaced at 18 threads per inch and are 0.012 inch diameter polypropylene filaments. The fill threads in the facing layers 14I and 14O are also 0.012 inch diameter polypropylene filaments and spaced at 18 threads per inch, and the warp threads in the facing layers are 18 threads per inch with each thread being 0.00875 inch diameter polyethylene. Such a fabric is commercially available from Synthetic Industries, Lumite Division, Norcross, Ga., under Style No. 60617000. In the industry, this is known as a "spacer" type weave.

With threads of the dimensions, spacing and pattern stated above, substantial open interstitial spaces are defined between the threads such that this is an "open weave" fabric. In general, an open weave fabric is defined as any fabric having open interstitial spaces between the threads which make up the fabric. Open weave fabrics are especially preferred for the core in a belt of the invention to provide light weight and ventilation.

A fabric for the core shown in FIG. 4 is also commercially available from Synthetic Industries, Lumite Division, as a "spacer" type weave. This fabric has the commercial designation Style No. 60645000. In this fabric, the cushion or middle layer 14M has warp and fill threads spaced at 26 threads per inch with the warp threads being 0.0117 inch diameter polypropylene filaments and the fill threads being 0.0096 inch diameter polypropylene filaments. The innerfacing layer 14'I has warp and fill threads spaced at 26 threads per inch with the warp threads being 0.010 inch diameter polyethylene filaments and the fill threads being 0.0096 inch diameter polypropylene filaments. The threads of the outer facing layer 14'O are 0.010 inch diameter polyethylene filaments spaced at 21 threads per inch in bundles of three threads so that there are seven bundles per inch.

It should be noted that the above two noted particular fabrics are just two of the possible fabrics which can be used to practice the invention and that other fabrics could be used to practice the invention.

The preferred core layer materials are fabrics made of synthetic thermoplastic threads. As such, the threads can be heated to their melting points and welded together. This is especially desirable to do at any cut edges of the core layer so as to join the ends of the threads together at the cut edges to prevent unravelling of the threads of the core. This is known in the industry as heat sealing the edges of the fabric and can be accomplished with any suitable heat source such as a radiant heat element, a heat gun or an open flame. It is particularly desirable with a three dimensional fabric core as described above to apply the binding strip 24 around its edges since the edges of the core, whether heat sealed or not, can be rather scratchy to a user.

In the belts 10 and 10' shown in FIGS. 1 and 2, the core layers are covered by inner and outer fabric layers. These fabric layers are preferably as described in U.S. Pat. No. 5,178,163, and in general are a stretchable or expandable fabric such as "Lycra", which is a trademark of E.I. Dupont de Nemours or a brushed polyester or nylon stretchable fabric. Although of a closed weave, the inner and outer layers of fabric are relatively breathable and allow for the passage of air and perspiration through them.

The core 14 or 14' can be secured to the layers 12, 12' and 14, 14' in any of a variety of ways. One such way is to create a fabric pocket by sewing the edges of the layers 12 and 14 together and then slipping the core inside the pocket before the pocket is completely sewn closed. Another way to secure the inner and outer fabric layers to the core is to directly sew the layers to the core. Still another way is to laminate the fabric layers to the core using a suitable hot or cold adhesive. Using a hot adhesive "flame combining" technique as described in U.S. Pat. No. 5,178,163 may be applied in some applications to laminate the fabric layers 12 and 16 to a three dimensional fabric core. After the body 26 of the belt is made (the body 26 includes the core 14, inner and outer layers 12 and 16 and the binding strip 24), the strap 18 is secured to the body 26 by sewing it thereto, preferably with two seams which extend substantially all the way around the body 26 near to the respective edges of the strap 18.

Figure 9:
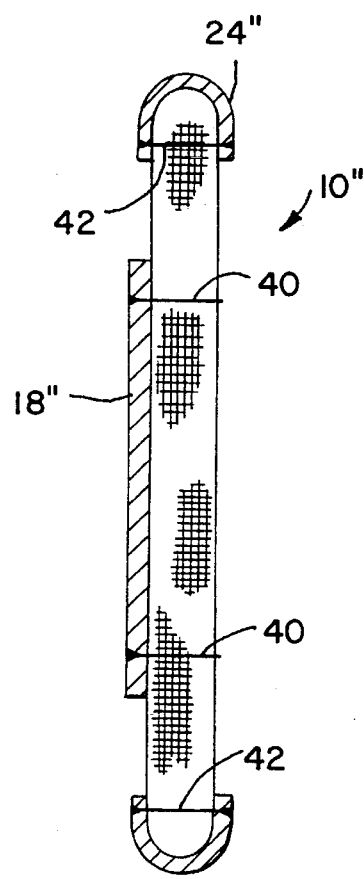
FIG. 9 is a schematic sectional view illustrating an alternate embodiment of the invention.

An alternate embodiment 10" shown in FIG. 9 is the same in all respects as the belts 10 and 10'. The embodiment 10" may be made with either of the three dimensional fabric cores 14 and 14' used in the belts 10 and 10' or with a different three dimensional fabric core. In FIG. 9, no inner or outer fabric layers corresponding to the layers 12 or 16 are provided. For comfort, the belt 10" is intended to be worn over the clothing of a user although, dependent upon the user's preference, it could be worn directly over the user's skin. The belt 10" is provided without inner or outer closed weave fabric layers so as to provide maximum ventilation through the belt. As shown in FIG. 9, the strap 18" is sewn to the core 14" along two spaced apart seams 40 and the binding strip 24" is also sewn to the edges of the core 14", shown by seam 42. Such seams 40 and 42 may also, of course, be used to make the belts 10 and 10'.

Many modifications and variations of the preferred embodiments described above will be apparent to those of ordinary skill in the art. For example, although in the preferred embodiments the corrugations of the cushion layers of the belt run in the direction of the length of the belt because the cushion layer is in general stiffer orthogonal to the corrugation direction, the corrugations could be oriented at a different angle relative to the length of the belt. Therefore, the invention should not be limited to the preferred embodiments described, but should be defined by the claims which follow.

I claim:

1. An abdominal support belt made of three dimensional fabric comprising:

a core including a cushion layer of open-weave fabric, said cushion layer having a serpentine undulating cross-sectional shape in a thickness dimension so as to define peaks and valleys in said dimension, said peaks and valleys spacing an inner surface of said core from an outer surface of said core such that the thickness of said core at a given location is greater than the sum of the thicknesses of threads of said fabric at said location, and said core includes two open-weave facing layers interwoven with said cushion layer, one said facing layer being on each of said opposed inner and outer surfaces of said core so that said cushion layer undulates between said facing layers, said facing layers each having an exposed surface;

a strap secured directly against said exposed surface of said one facing layer on the outer surface of said core, said strap being narrower and longer than said core and overlying said outer surface of said core; and means for securing said strap around a body with said core between said strap and said body and said exposed surface of said one facing layer on the inner surface of said core being directly against said body.

2. A support belt as in claim 1, further comprising a fabric binding strip around the edges of said core spanning the inner and outer surfaces of said core.

* * * * *